United States Patent
Woodward et al.

(10) Patent No.: US 7,186,744 B2
(45) Date of Patent: Mar. 6, 2007

(54) PROSTAMIDES FOR THE TREATMENT OF GLAUCOMA AND RELATED DISEASES

(75) Inventors: David F. Woodward, Lake Forest, CA (US); Robert M. Burk, Laguna Beach, CA (US)

(73) Assignee: Allergan, Inc., Irvine, CA (US)

( * ) Notice: Subject to any disclaimer, the term of this patent is extended or adjusted under 35 U.S.C. 154(b) by 432 days.

(21) Appl. No.: 10/713,500

(22) Filed: Nov. 13, 2003

(65) Prior Publication Data

US 2005/0107463 A1  May 19, 2005

(51) Int. Cl.
*A61K 31/404* (2006.01)
*C07D 209/18* (2006.01)

(52) U.S. Cl. ............... 514/415; 548/504; 548/507

(58) Field of Classification Search ........... 548/504, 548/507; 514/415
See application file for complete search history.

(56) References Cited

U.S. PATENT DOCUMENTS

| | | | | |
|---|---|---|---|---|
| 5,688,819 | A | 11/1997 | Woodward et al. | ......... 514/357 |
| 6,376,533 | B1 | 4/2002 | Burk et al. | |
| 6,410,591 | B1 | 6/2002 | Burk et al. | |
| 6,531,504 | B2 | 3/2003 | Burk et al. | |
| 6,538,018 | B1 | 3/2003 | Burk et al. | |
| 6,586,462 | B2 | 7/2003 | Burk et al. | |

FOREIGN PATENT DOCUMENTS

| | | |
|---|---|---|
| EP | 0 458 587 A1 | 11/1991 |
| JP | 50013363 A2 * | 2/1975 |
| WO | WO 03/047417 A2 | 6/2003 |

OTHER PUBLICATIONS

Dragoli, D.R., et al., *Parallel Synthesis of Prostaglandin E1 Analogues*, J. Comb. Chem 1999, 1. p. 534-539.

Bezuglov, et al., Synthesis and Biological Evaluation of Novel Amides of Polyunsaturated Fatty Acids with Dopamine, *Bioorganic & Medicinal Chemistry Letters* 11 (2001), 447-449).

Bezuglov, V.V., et al. Bioactive Amides of Fatty Acids, *Biochemistry* (Moscow), vol. 63, No. 1 1998, pp. 22-30.

Bezuglov, V.V., et al., Arachidonoylcholine and N,N-dimethylaminoethyl arachidonate, new cholinergic compounds, *Russian Journal of Bioorganic Chemistry*, vol. 27, No. 3, 2001, pp. 200-203.

Bezuglov, V.V., et al., Stereochemistry of substitution of allylic hydroxyl with fluorine in prostaglandins. *Russian Journal of bioorganic Chemistry*, vol. 22, No. 10, 1996, pp. 688-695.

Bezuglov, V.V., et al., Synthesis of novel coumarin-3-carboxylic acid derivatives as chemical detectors of hydroxyl radicals in biological systems, *Russian Journal of Bioorganic Chemistry*, vol. 23, No. 4, 1997, pp. 288-291.

Bisogno, T., et al., N-acyl-dopamines: novel synthetic CB1 cannabinoid-receptor ligands and inhibitors of anandamide inactivation with cannabimimetic activity in broto and in vivo, *Biochem J.*, 2000, 351, pp. 817-824.

Bito, L.Z., Prostaglandins, other eicosanoids, and their derivatives as potential antiglaucoma agents, Chpt. 20, *Applied Pharmacology in the medical treatment of glaucoma*, Drance, S.M. et al., NY, Grune & Stratton, 1984, pp. 477-505.

Bito, L.Z., Prostaglandins Old concepts and new perspectives, *Arch Ophthalmol*, vol. 105, pp. 1036-1039 (1987).

English, D., et al., Messenger functions of phosphatidic acid, *Chemistry of physics of lipids*, 80, 1996, 117-132.

Janusz, J. M. et al., Vanilloids. 1. analogs of capsaicin with antinociceptive and anti-inflammatory activity, *J. Med Chem.* 1993, 2595-2604.

Kulikov, V.I., et al., Bioactive amide of prostaglandin E1 and ethanolamine plasmalogen analog of platelet-activating factor inhibits several pathways of human platelet aggregation, *Biochemistry* (Moscow), vol. 65, No. 4, 2000 pp. 427-430.

Nilsson, S., et al., PGF2 increases uveoscleral outflow, *Invest Ophthalmic Vis Sci.* (suppl)284 ARVO Abstracts, 1987.

Siebold, et al., Esterfied prostaglandin shows 'potent' promise, *Prodrug*, (5) 3 (1989).

Wartmann, M., et al., The MAP kinase signal transduction pathway is activated by the endogenous cannabinoid anandamide, *FEBS Letters*, 359, 1995, 133-136.

* cited by examiner

*Primary Examiner*—Rebecca Anderson
(74) *Attorney, Agent, or Firm*—Brent A. Johnson; Robert J. Baran; Martin A. Voet

(57) ABSTRACT

Disclosed herein are compositions comprising an amide related to a prostaglandin and an amine wherein the amine is selected from the group consisting of epinephrine, dopamine, serotonin, and analogs or prodrugs thereof. Also disclosed are certain chemical compounds, pharmaceutical compositions, and methods of treating glaucoma.

9 Claims, No Drawings

PROSTAMIDES FOR THE TREATMENT OF GLAUCOMA AND RELATED DISEASES

FIELD OF THE INVENTION

The present invention relates to novel amides related to prostaglandins as potent ocular hypotensives that are particularly suited for the management of glaucoma and related diseases.

BACKGROUND OF THE INVENTION

Description of the Related Art

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage. Considering all types together, glaucoma occurs in about 2% of all persons over the age of 40 and may be asymptotic for years before progressing to rapid loss of vision.

Certain eicosanoids and their derivatives have been reported to possess ocular hypotensive activity, and have been recommended for use in glaucoma management. Eicosanoids and derivatives include numerous biologically important compounds such as prostaglandins and their derivatives. Prostaglandins can be described as derivatives of prostanoic acid which have the structural formula:

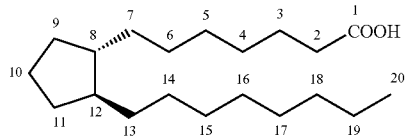

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by a or α or β [e.g. prostaglandin $F_{2\alpha}$ ($PGF_{2\beta}$)].

Prostaglandins were earlier regarded as potent ocular hypertensives, however, evidence accumulated in the last decade shows that some prostaglandins are highly effective ocular hypotensive agents, and are ideally suited for the long-term medical management of glaucoma (see, for example, Bito, L. Z. *Biological Protection with Prostaglandins*, Cohen, M. M., ed., Boca Raton, Fla, CRC Press Inc., 1985, pp. 231–252; and Bito, L. Z., *Applied Pharmacology in the Medical Treatment of Glaucomas Drance*, S. M. and Neufeld, A. H. eds., New York, Grune & Stratton, 1984, pp. 477–505. Such prostaglandins include $PGF_{2\alpha}$, $PGF_{1\alpha}$, $PGE_2$, and certain lipid-soluble esters, such as $C_1$ to $C_2$ alkyl esters, e.g. 1-isopropyl ester, of such compounds.

Although the precise mechanism is not yet known, experimental results indicate that the prostaglandin-induced reduction in intraocular pressure results from increased uveoscleral outflow [Nilsson et. al., *Invest. Ophthalmol. Vis. Sci.* (suppl), 284 (1987)].

The isopropyl ester of $PGF_{2\alpha}$ has been shown to have significantly greater hypotensive potency than the parent compound, presumably as a result of its more effective penetration through the cornea. In 1987, this compound was described as "the most potent ocular hypotensive agent ever reported" [see, for example, Bito, L. Z., *Arch. Ophthalmol.* 105, 1036 (1987), and Siebold et al., *Prodrug* 5 3 (1989)].

Whereas prostaglandins appear to be devoid of significant intraocular side effects, ocular surface (conjunctival) hyperemia and foreign-body sensation have been consistently associated with the topical ocular use of such compounds, in particular $PGF_{2\alpha}$ and its prodrugs, e.g., its 1-isopropyl ester, in humans. The clinical potentials of prostaglandins in the management of conditions associated with increased ocular pressure, e.g. glaucoma are greatly limited by these side effects.

U.S. Pat. No. 5,688,819, commonly assigned to Allergan, Inc., and incorporated herein by reference discloses compounds known as prostamides. Prostamides are distinguished from prostaglandins in that the oxygen which is bonded to carbonyl group is replaced by a nitrogen bearing substituent. Those skilled in the art will readily recognize that this replacement significantly alters several electronic and steric properties of an important structural feature in the biological molecule. Significantly, it is commonly believed in the art that resonance between the nitrogen lone pair and the carbonyl π-bond is significantly greater than resonance between the carbonyl group and an oxygen lone pair in a carboxylic ester or a carboxylic acid. This belief is supported by the well established experimental observation that the nitrogen atom in an amide is planar, as opposed to the pyramidal geometry of an amine. Thus, the commonly accepted belief in the art is that the nitrogen atom of an amine is sp$^3$ hybridized, while nitrogen atom of an amide is sp$^2$ hybridized, with the bonded electrons occupying the sp$^2$ hybrid orbitals and the nonbonded electron pair occupying a p orbital to allow for conjugation with the carbonyl π system. By contrast, the hybridization, bonding, and geometry of the electrons of the oxygen atom in water and alcohols are very similar to those of carboxylic acids or carboxylic esters.

The increased resonance between the nitrogen and the carbonyl group in the amide confers several unique properties to the molecule. First, it is well known in the art that hydrolysis of amides is at least two orders of magnitude slower than the hydrolysis of esters (see, for example, Francis A. Carey, Organic Chemistry, New York: McGraw-Hill Book Company, 1987, p. 779). Thus, hydrolysis of amides in vivo is slowed to such an extent that a prostamide cannot be considered to be a prodrug of a prostaglandin. Second, the increased resonance significantly increases the barrier to rotation about the nitrogen-carbonyl sigma bond relative to the analogous rotational barrier associated with esters and carboxylic acids. Thus, a prostamide has a sterically significant, stable, rigid group replacing the oxygen atom of the prostaglandin. This significant steric difference will have a significant effect in binding to a number of receptor sites since geometry is important for many receptor sites. Since the carboxylic acid group of a prostaglandin is a polar, ionizable, group, with four potential hydrogen bond receiving electron pairs, and in the case of the protonated acid, one potential hydrogen bond donor, it is reasonable for a person of ordinary skill in the art to believe that this functional group will be important to the binding of the molecule to a number of receptors. It follows that changing the resonance properties, the hybridization of the bonding and nonbonding electrons, the geometry of the nitrogen atom, the number of available hydrogen bonding sites, and the electronegativity of the of the nitrogen relative to oxygen, will confer significantly different biological properties to prostamides relative to prostaglandins.

Recently, it is becoming more commonly accepted in the art that amides have distinct properties over carboxylic acids. For example, it has been shown that anandamide, a common amide of arachidonic acid, has significant biological activity that arachidonic acid does not. Other work has also been done to show that amides have distinct activity as compared to carboxylic acid, which has caused some in the field to classify fatty acid amides as "a new family of biologically active lipids" (Bezuglov, et. al., "Synthesis and Biological Evaluation of Novel Amides of Polyunsaturated Fatty Acids with Dopamine", Bioorganic & Medicinal Chemistry Letters 11 (2001), 447–449).

It has been shown that prostamides have pronounced effects on smooth muscle and are potent ocular hypotensive agents. Additionally, prostamides cause significantly lower ocular surface hyperemia than prostaglandins. One prostamide exemplary of the these effects is bimatoprost, which is marketed by Allergan, Inc. under the trade name Lumigan®, which has the structure shown in Formula I below.

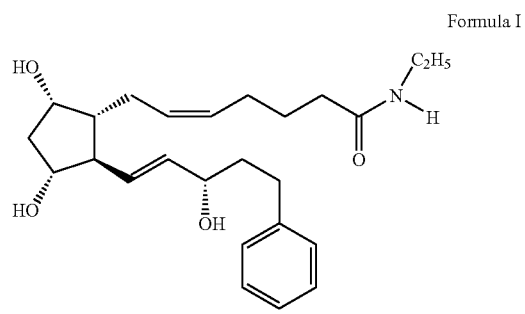

Formula I

SUMMARY OF THE INVENTION

Embodiments disclosed herein relate to a composition comprising an amide related to a prostaglandin and an amine selected from the group consisting of epinephrine, dopamine, diacetyl doparnine and serotonin.

Another aspect of this invention relates to a compound comprising

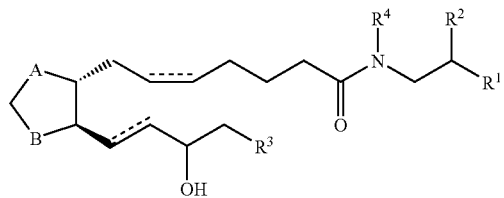

or a salt, ester, or prodrug thereof,
wherein
said compound is not naturally occurring;
the hatched wedge indicates an α configuration and the solid wedge indicates a β configuration;
the dashed line indicates the presence or absence of a double bond;
A and B are both CHOH, or A is CHOH and B is C=O, or B is CHOH and A is C=O;
$R^1$ is phenyl, indolyl, or monohydroxy or dihydroxy derivatives of phenyl or indolyl;
$R^2$ is OH or H;
$R^3$ is n-butyl, n-pentyl, or n-hexyl; cyclohexyl, Ar, or W—Ar;
wherein Ar is phenyl, naphthyl, thienyl, furanyl, or benzothienyl, or a substituted derivative of phenyl, naphthyl, thienyl, furanyl, or benzothienyl, wherein from 1 to 3 hydrogen atoms are substituted with halogen, methyl, or trifluoromethyl; and
W is N, S, O, or $CH_2$; and
$R^4$ is hydrogen, methyl, ethyl, iso-propyl, or n-propyl.

Other aspects of this invention are related to ophthalmic compositions comprising a therapeutically active agent or a prodrug thereof. In these compositions said therapeutically active agent comprises an amide functional group, and selective hydrolysis of said amide functional group of the therapeutically active agent produces 1) a compound having agonist activity at a prostaglandin receptor and 2) a compound selected from the group consisting of serotonin and analogs thereof, dopamine and analogs thereof, and epinephrine and analogs thereof.

Other embodiments of this invention are related to a method of treating glaucoma. This method comprises administering to a mammal suffering from glaucoma an effective amount of a therapeutically active agent or a pharmaceutically acceptable salt or a prodrug thereof, said therapeutically active agent consisting of a prostaglandin and a 2-aryl-1-ethylamine coupled by an amide bond.

DETAILED DESCRIPTION OF THE INVENTION

The term "prostaglandin" referred to herein should be interpreted broadly as a natural prostaglandin, a prostaglandin analog, a prostaglandin receptor agonist, or a prodrug, a salt, or a salt of a prodrug of any of the previous three types of compounds. A natural prostaglandin is defined as one of several prostaglandin compounds that are produced in living organisms. The structural formula previously depicted is represented below in a modified form for clarification purposes to aid in understanding certain claim elements used herein.

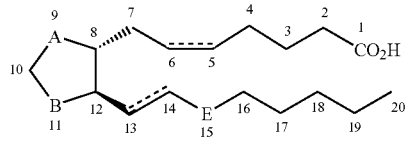

In reference to the compounds related to this invention herein, the term "α chain" refers to the top chain which is formed by the carbon atoms referred to as 1–7 in the structure above. The term "ω chain" refers to the bottom chain which is formed by the carbon atoms referred to as 13–20 in the structure above. The ring formed by the carbon atoms referred to as 8–12 will be referred to as the "cyclopentyl ring" herein for convenience. The letters A, B, and E indicate carbons which have particular functional groups in the natural prostaglandins. A and B can be either CHOH or C=O, depending upon the particular natural prostaglandin, and E is CHOH where the OH is in the α-configuration (points downward). The dashed lines indicate where double bonds are present in certain of the natural prostaglandins.

Three classes of natural prostaglandins of particular interest herein are prostaglandin E, prostaglandin F, and prostaglandin D. All of the compounds known collectively as prostaglandin E are characterized by the common features that A is C=O and B is CHOH, where the OH is in the α-configuration. One prostaglandin E which is of interest herein is prostaglandin $E_1$, which has a single covalent bond between carbons 5 and 6 and a double covalent bond between carbons 13 and 14. Another prostaglandin E of interest herein is prostaglandin $E_2$, which has a double covalent bond between carbons 5 and 6 and a double covalent bond between carbons 13 and 14. Thus, the subscript designates the number of carbon-carbon double bonds found in the basic prostaglandin structure.

The compounds known collectively as prostaglandin F are characterized by the common features that both A and B are CHOH. Similar to prostaglandin E the OH is in the α-configuration for B, but the configuration of the OH of A is designated by a subscript. Thus, prostaglandin $F_{2\alpha}$, which is of particular interest herein, is a prostaglandin F which has the OH of B in the α-configuration, and similar to prostaglandin $E_2$, prostaglandin $F_{2\alpha}$ has two double covalent carbon-carbon bonds between carbons 5 and 6 and carbons 13 and 14.

The compounds known collectively as prostaglandin D are characterized by the common features that A is CHOH, where the OH is in the α-configuration, and B is C=O. Similar to the previous examples, one prostaglandin D of interest herein is designated prostaglandin $D_2$, which indicates that the compound has two double covalent carbon-carbon bonds between carbons 5 and 6 and carbons 13 and 14.

A "prostaglandin analog" as used herein refers to a compound having certain structural similarities to the natural prostaglandins. An analog has all of the features of that natural prostaglandin related to A, B, and E, including stereochemistry, and the presence or absence of double bonds at carbons 5, 6, 13 and 14, or reasonable equivalents of those features. A reasonable equivalent to a feature is a feature that a person of ordinary skill in the art would reasonably consider to have a similar purpose, but might enhance the properties of the compound. While not intending to limit the scope of the invention in any way, in general, an atom or functional group which is isovalent or isoelectronic with the atom or functional group it is replacing would be a reasonable equivalent. Thus, for example, an α-CHSH group is a reasonable equivalent for an α-CHOH group, and a C=S group is a reasonable equivalent for a C=O group. Another type of reasonable equivalent has different electronic properties but similar steric properties to the group it is replacing. Thus, F is a reasonable equivalent for H and $OCH_3$ is a reasonable equivalent for OH.

Beyond the similarities for A, B, E and the double bonds indicated, a prostaglandin analog will have a cyclopentyl ring, an α-chain, and an ω-chain which are attached to adjacent atoms on the cyclopentyl ring. The meanings of the cyclopentyl ring and the α and ω chains for prostaglandin analogs are broader than those of the natural prostaglandins. For a prostaglandin analog, the "cyclopentyl ring" is a five-membered ring consisting of three or more carbon atoms, the "α-chain" has between 4 and 12 carbon atoms and the "ω-chain" has between 4 and 20 carbon atoms. Either chain may comprise double or triple covalent bonds, aromatic or aliphatic rings, and heteroatoms such as S, O, N, and halogens. The only stereochemical requirements of prostaglandin analogs are the same as those of the natural prostaglandins they are associated with. Thus, for a prostaglandin E analog, B and E should be CHOH with the OH in the α-configuration, and the α- and ω-chains should have the α and β configurations respectively with relation to the connection to the cyclopentyl ring. The table below lists features which would be present in analogs of several types of natural prostaglandins. Alternatively, a reasonable equivalent for each feature might be present in the given prostaglandin analog.

| Prostaglandin Analog | A | B | E | C5–C6 | C13–C14 |
|---|---|---|---|---|---|
| E | C=O | CH(OH) α conf | CH(OH) α conf | NA | NA |
| $E_1$ | C=O | CH(OH) α conf | CH(OH) α conf | single bond | trans double bond |
| $E_2$ | C=O | CH(OH) α conf | CH(OH) α conf | cis double bond | trans double bond |

-continued

| Prosta-glandin Analog | A | B | E | C5–C6 | C13–C14 |
|---|---|---|---|---|---|
| F | CH(OH) α conf | CH(OH) α conf | CH(OH) α conf | NA | NA |
| $F_{2\alpha}$ | CH(OH) α conf | CH(OH) α conf | CH(OH) α conf | cis double bond | trans double bond |
| D | CH(OH) α conf | C=O | CH(OH) α conf | NA | NA |
| $D_2$ | CH(OH) α conf | C=O | CH(OH) α conf | cis double bond | trans double bond |

NA means there is no requirement.

"A prostaglandin receptor agonist" refers to a compound which binds to and activates one of the prostaglandin receptors at a concentration of less than $10^4$ nanomolar according to the Radioligand Binding and the FLIPR™ assay described hereafter. Of particular interest herein are compounds having agonist activity at an FP receptor, an $EP_1$ receptor, an $EP_2$ receptor, an $EP_4$ receptor, and/or a DP receptor.

Radioligand Binding

Cells Stably Expressing $EP_1$, $EP_2$, $EP_4$ and FP Receptors

HEK-293 cells stably expressing the human or feline FP receptor, or $EP_1$, $EP_2$, or $EP_4$ receptors were washed with TME buffer, scraped from the bottom of the flasks, and homogenized for 30 sec using a Brinkman PT 10/35 polytron. TME buffer was added to achieve a final 40 ml volume in the centrifuge tubes (the composition of TME is 100 mM TRIS base, 20 mM $MgCl_2$, 2M EDTA; 10N HCl is added to achieve a pH of 7.4).

The cell homogenate was centrifuged at 19000 r.p.m. for 20 min at 4° C. using a Beckman Ti-60 rotor. The resultant pellet was resuspended in TME buffer to give a final 1 mg/ml protein concentration, as determined by Biorad assay. Radioligand binding competition assays vs. [$^3$H-] 17-phenyl $PGF_{2\alpha}$ (5 nM) were performed in a 100 μl volume for 60 min. Binding reactions were started by adding plasma membrane fraction. The reaction was terminated by the addition of 4 ml ice-cold TRIS-HCl buffer and rapid filtration through glass fiber GF/B filters using a Brandel cell harvester. The filters were washed 3 times with ice-cold buffer and oven dried for one hour.

[$^3$H—] $PGE_2$ (specific activity 180 Ci mmol) was used as the radioligand for EP receptors. [$^3$H] 17-phenyl $PGF_{2\alpha}$ a was employed for FP receptor binding studies. Binding studies employing $EP_1$, $EP_2$, $EP_4$ and FP receptors were performed in duplicate in at least three separate experiments. A 200 μl assay volume was used. Incubations were for 60 min at 25° C. and were terminated by the addition of 4 ml of ice-cold 50 mM TRIS-HCl, followed by rapid filtration through Whatman GF/B filters and three additional 4 ml washes in a cell harvester (Brandel). Competition studies were performed using a final concentration of 5 nM [$^3$H]—$PGE_2$, or 5 nM [3H] 17-phenyl $PGF_{2\alpha}$ and non-specific binding determined with $10^{-5}$M of unlabeled $PGE_2$, or 17-phenyl $PGF_{2\alpha}$, according to receptor subtype studied.

Cells Transiently Expressing $EP_3$ Receptors

COS-7 cells were transiently transfected with $pcDNA_3$ containing cDNA for the $EP_{3D}$ receptor by employing lipofectin. For radioligand binding the cells were harvested after 2 days. Plasma membrane preparations for each of the transient transfectants is as follows. COS-7 cells were washed with TME buffer, scraped from the bottom of the flasks, and homogenized for 30 sec using a Brinkman PT 10/35 polytron. TME buffer was added to achieve a final 40 ml volume in the centrifuge tubes.

The cell homogenate was centrifuged at 19000 r.p.m. for 20 min at 4° C. using a Beckman Ti-60 rotor. The resultant pellet was resuspended in TME buffer to give a final 1 mg/ml protein concentration, as determined by Biorad assay. Radioligand binding assays were performed in a 200 μl volume, as described above for other EP receptors.

Cells Transiently Expressing TP Receptors

COS-7 cells were transiently transfected with $pcDNA_3$ containing cDNA for the TP receptor using methods as described for transient $EP_3$ receptor transfectants. Plasma membrane preparations for the transient transfectants and radioligand binding methods were the same as for the $EP_3$ receptor methods. The binding of [$^3$H]-SQ29548 (specific activity 41.5 Ci $mmol^{-1}$) at TP receptors was determined in duplicate in at least three separate experiments. Incubations were for 60 min at 25° C. and were terminated by the addition of 4 ml of ice-cold 50 mM TRIS-HCl, followed by rapid filtration through Whatman GF/B filters and three additional 4 ml washes in a cell harvester (Brandel). Competition studies were performed using a final concentration of 5 nM [$^3$H]-SQ 29548 and non-specific binding determined with $10^{-5}$ M of unlabeled SQ 29548.

Methods for FLIPR™ Studies (a) Cell Culture

HEK-293(EBNA) cells, stably expressing one type or subtype of recombinant human prostaglandin receptors (prostaglandin receptors expressed: hDP/Gqs5; $hEP_1$; $hEP_2$/Gqs5; $hEP_{3A}$/Gqi5; $hEP_4$/Gqs5; hFP; hIP; hTP), were cultured in 100 mm culture dishes in high-glucose DMEM medium containing 10% fetal bovine serum, 2 mM 1-glutamine, 250 μg/ml geneticin (G418) and 200 μg/ml hygromycin B as selection markers, and 100 units/ml penicillin G, 100 μg/ml streptomycin and 0.25 μg/ml amphotericin B.

(b) Calcium Signal Studies on the FLIPR™

Cells were seeded at a density of $5 \times 10^4$ cells per well in Biocoat® Poly-D-lysine-coated black-wall, clear-bottom 96-well plates (Becton-Dickinson) and allowed to attach overnight in an incubator at 37° C. Cells were then washed two times with HBSS-HEPES buffer (Hanks Balanced Salt Solution without bicarbonate and phenol red, 20 mM HEPES, pH 7.4) using a Denley Cellwash plate washer (Labsystems). After 45 minutes of dye-loading in the dark, using the calcium-sensitive dye Fluo-4 AM at a final concentration of 2 μM, plates were washed four times with HBSS-HEPES buffer to remove excess dye leaving 100 μl in each well. Plates were re-equilibrated to 37° C. for a few minutes.

Cells were excited with an Argon laser at 488 nm, and emission was measured through a 510–570 nm bandwidth emission filter (FLIPR™, Molecular Devices, Sunnyvale, Calif.). Drug solution was added in a 50 μl volume to each well to give the desired final concentration. The peak increase in fluorescence intensity was recorded for each well. On each plate, four wells each served as negative (HBSS-HEPES buffer) and positive controls (standard agonists: BW245C (hDP); $PGE_2$ ($hEP_1$; $hEP_2$/Gqs5; $hEP_{3A}$/

Gqi5; hEP$_4$/Gqs5); PGF$_{2\alpha}$ (hFP); carbacyclin (hIP); U-46619 (hTP), depending on receptor). The peak fluorescence change in each drug-containing well was then expressed relative to the controls.

Compounds were tested in a high-throughput (HTS) or concentration-response (CoRe) format. In the HTS format, forty-four compounds per plate were examined in duplicates at a concentration of $10^{-5}$ M. To generate concentration-response curves, four compounds per plate were tested in duplicates in a concentration range between $10^{-5}$ and $10^{-11}$ M. The duplicate values were averaged. In either, HTS or CoRe format each compound was tested on at least 3 separate plates using cells from different passages to give an $n \geq 3$.

In addition to those aspects of prostaglandins in the aforementioned disclosure, certain other features of particular interest in relation to the prostaglandins are contemplated herein. In certain useful embodiments disclosed herein, the prostaglandin comprises from 0 to 2 double covalent bonds connecting two carbon atoms. In other embodiments, the prostaglandin comprises two double covalent bonds connecting two carbon atoms. In other useful embodiments, the prostaglandin comprises from 1 to 3 heteroatoms, wherein said heteroatoms comprise S or O, said heteroatoms replacing carbon atoms which are present in prostaglandin E$_2$, prostaglandin F$_2$, or prostaglandin D$_2$. Of particular interest herein are compounds related to a prostaglandin comprising a moiety which replaces from 2 to 5 carbon atoms on the terminal end of a ω chain of a natural prostaglandin, said moiety comprising phenyl, naphthyl, benzothienyl, furanyl, or thienyl.

The terms "FP-related", "EP$_1$-related", "EP$_2$-related", "EP$_4$-related", and "DP-related", are generic terms used to classify prostaglandin compounds. The term "FP-related" refers to a compound which is an FP receptor agonist, a prostaglandin F, a prostaglandin F analog, or a salt or prodrug of one of those compounds. Similarly, the term "EP$_1$-related" refers to a compound which is an EP$_1$ receptor agonist, a prostaglandin E, a prostaglandin E analog, or a salt or prodrug of one of those compounds. The term "EP$_2$-related" refers to a compound which is an EP$_2$ receptor agonist, a prostaglandin E, a prostaglandin E analog, or a salt or prodrug of one of those compounds. The term "EP$_4$-related" refers to a compound which is an EP$_4$ receptor agonist, a prostaglandin E, a prostaglandin E analog, or a salt or prodrug of one of those compounds. The term "DP-related" refers to a compound which is an DP receptor agonist, a prostaglandin D, a prostaglandin D analog, or a salt or prodrug of one of those compounds.

The term "prodrug" used in relation to a natural prostaglandin, a prostaglandin analog, or a prostaglandin receptor agonist has the meaning normally understood in the art. That is, the prodrug is a compound which readily decomposes in vivo to form a natural prostaglandin, a prostaglandin analog, or a prostaglandin receptor agonist. While not intending to limit the scope of the invention in any way, one common type of prodrug is an ester which hydrolyzes to yield an active compound with a hydroxyl functional group.

The term "salt" has the meaning normally understood by those of ordinary skill in the art. A "pharmaceutically acceptable salt" is any salt that retains the activity of the parent compound and does not impart any deleterious or untoward effect on the subject to which it is administered and in the context in which it is administered.

Pharmaceutically acceptable salts of acidic functional groups may be derived from organic or inorganic bases. The salt may be a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

The definition of the terms natural prostaglandin, prostaglandin analog, a prostaglandin receptor agonist, prodrug, and salts given herein are intended only to clarify the meaning of certain claim elements and are not intended to narrow in any way the overall scope of the claims taken as a whole.

As mentioned previously, certain claims relate to a composition comprising an amide related to a prostaglandin and an amine selected from the group consisting of epinephrine, dopamine, diacetyl dopamine, and serotonin. The term "amide" used herein has the meaning normally understood by those of ordinary skill in the art of organic chemistry, as a chemical compound having an amide functional group. An amide functional group, as understood by those of ordinary skill in the art, comprises a carbonyl (C=O) group where the carbonyl carbon is directly bonded to a nitrogen atom related to an amine. This means that when the amide is formed, the carbon atom of the carbonyl group replaces one of the hydrogen atoms of the amine, and the nitrogen of the amine replaces one of the moieties attached to the carbonyl group.

The bond between the carbonyl carbon and the nitrogen atom related to the amine is referred to as an "amide bond". This description of the amide, the amide functional group, and the amide bond is purely a mental exercise and is not meant to be necessarily related to how the amide is actually formed. Thus, the amide may be formed by a number means other than by the formation of an amide bond, such as by oxidation of an amine, and the amide bond may not have been formed at all, but may simply exist because a compound is an amide.

The term "related to" used with reference to a prostaglandin and an amide refers to the fact that an amide bond is formed between the two using the mental exercise just described, that is one of the moieties attached to the carbonyl and one of the hydrogen atoms attached to the amine nitrogen are replaced with a direct bond between the carbonyl carbon and the nitrogen. As mentioned, the amide is a product of a mental exercise, and the term "related to" should not be construed as meaning that the compound is necessarily prepared from the prostaglandin and the amine or related compounds thereof. In fact, those skilled in the art will recognize that an amide "related to" a prostaglandin and an amine may be prepared without forming either molecule. In addition, the term "related to" refers to the fact that the amide might be a prodrug of the molecule that results from the formation of an amide bond between the amine and the prostaglandin. The term "related to" also recognizes that the prostaglandin may be a carboxylic acid, or an ester, or some other derivative of a carboxylic acid such as a nitrile. Thus, "related to" describes the prostaglandin and the amine related to the amide, and recognizes that certain minor and easily reversible changes may have been made to certain oxygen, nitrogen, or sulfur containing functional groups, and that no change in the carbon-carbon bonding is made to either the prostaglandin or the amine.

In reference to an amide functional group related to the present claims, the term "selective hydrolysis of said amide functional group" refers to a mental exercise wherein the amide functional group is hydrolyzed with a water molecule or a hydroxide ion to form a carboxylic acid, or a salt of a carboxylic acid, and an amine. It is not necessary that a particular amide under consideration be capable of selective hydrolysis at the amide functional group since the hydrolysis is strictly a mental exercise.

Amines of interest herein include serotonin and analogs thereof, dopamine and analogs thereof, and epinephrine and analogs thereof. In the case of these amines, an analog is a compound having the same basic structure as the parent, that is an aromatic ring linked to a nitrogen atom by an ethylene moiety, but having one or two of the following changes: 1) adding or subtracting one or two atoms or methylene groups from the ethylene linker attaching the nitrogen to the aromatic ring, 2) substituting one or more oxygen atoms with sulfur atoms, 3) substituting one or more hydrogen atoms with fluorine atoms, 4) adding 1–3 additional substituents to the aromatic ring, 5) removing one or more hydroxyl moieties, 6) adding or removing a $C_{1-3}$ alkyl moiety to or from the nitrogen, and 7) changing an alkyl group on the nitrogen by adding or removing one or two carbon atoms and the associated hydrogen atoms.

The term "2-aryl-1-ethylamine" used with respect to certain embodiments disclosed herein refers to a primary or secondary amine where the nitrogen of the amine is linked to an aromatic ring by an ethylene group. This means that the two groups are attached to opposite ends (different carbon atoms) of the ethylene group. Furthermore, the ethylene group and the aromatic ring may optionally have one or more hydroxyl or acyloxy moieties attached, where a hydrogen atom is replaced by a hydroxyl (OH) moiety. In certain embodiments, the 2-aryl-1-ethylamine comprises from 1 to 3 hydroxy or acyloxy moieties.

The amides disclosed herein can be prepared by a number of methods well known in the art. While not intending to limit the scope of the claims in any way, one convenient method of preparing these compounds is by reacting a prostaglandin having a carboxylic acid moiety with the amine in the presence of an appropriate catalyst and an appropriate base, to form the amide. While not intending to limit the scope of the invention in any way, examples of useful procedures for preparing amides are provided herein. In many cases, it is necessary to protect certain functional groups on the amine and prostaglandin in order to carry out the amidation reaction. The use of protecting groups to accomplish this objective is well known in the art and well within the skill of one of ordinary skill in the art of organic chemistry, and an example of a protection process is disclosed in one of the examples herein. The amines and the prostaglandins of the present invention can be prepared by methods well known in the art, purchased, or in some cases, may be isolated from natural sources. For example, the following U.S. Patents, incorporated herein by reference, describe methods for preparing various prostaglandin compounds: U.S. Pat. Nos. 6,586,462; 6,538,018; 6,531,504; 6,410,591; 6,376,533; and 5,688,819. Although the use of the amidation reaction is a convenient way to prepare the amides related to this invention in many instances, it is described herein to demonstrate that the preparation of compounds related to this invention can be carried out by methods well known in the art and it is not meant to limit the scope of the claims in any way.

In other embodiments of particular interest herein the prostaglandin is prostaglandin $F_{2\alpha}$ and the amine is dopamine. In other embodiments of particular interest herein the prostaglandin is prostaglandin $F_{2\alpha}$ and the amine is diacetyl dopamine. In other embodiments of particular interest herein the prostaglandin is prostaglandin $F_{2\alpha}$ and the amine is serotonin. In other embodiments of particular interest herein the prostaglandin is prostaglandin $F_{2\alpha}$ and the amine is epinephrine.

In relation to the compounds comprising

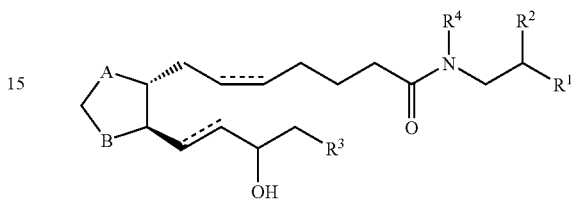

which were disclosed previously herein, of particular interest are compounds wherein $R^3$ is n-butyl, Ar, or W—Ar, with Ar being phenyl, naphthyl, or benzothienyl. Of exceptional interest are those compounds wherein Ar is phenyl, particularly in the cases that W is O or $CH_2$.

In other embodiments related to the aforementioned compounds, $R^1$ is 3,4-dihydroxyphenyl and $R^2$ is OH.

In other embodiments related to the aforementioned compounds, $R^1$ is 3,4-dihydroxyphenyl, $R^2$ is OH, and $R^4$ is methyl.

In other embodiments related to the aforementioned compounds, $R^1$ is 3,4-dihydroxyphenyl, $R^2$ is H, and $R^4$ is hydrogen.

In other embodiments related to the aforementioned compounds, $R^1$ is 5-hydroxyindolyl, $R^2$ is H, and $R^4$ is hydrogen.

The following compounds are also of interest

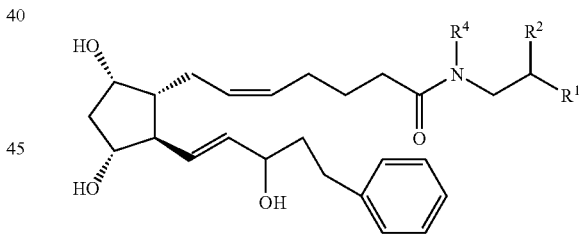

where $R^1$, $R^2$, and $R^4$ are the moieties previously described.

The following compounds 1–3 are also useful for the purposes described herein:

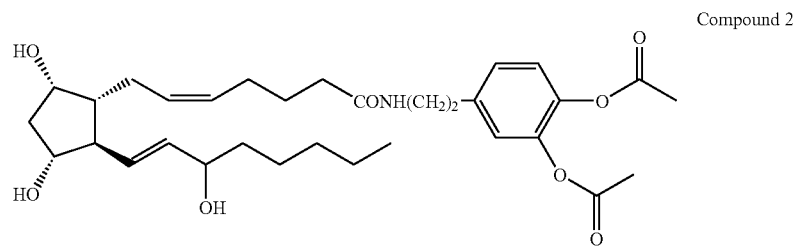

Compound 2

Acetic acid 2-acetoxy-5-(2-{(Z)-7-[(1R,2R,3R,5S)-3,5-dihydroxy-2-((E)—(S)-3-hydroxy-oct-1-enyl)-cyclopenyl]-hept-5-enoylamino}-ethyl)-phenyl ester Compound 2

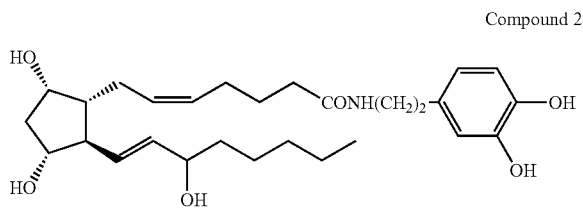

(Z)-7-[(1R,2R,3R,5S)-3,5-Dihydroxy-2-((E)—(S)-3-hydroxy-oct-1-enyl)-cyclopentyl ]-hept-5-enoic acid [2-(3,4-dihydroxy-phenyl)-ethyl]-amide Compound 3

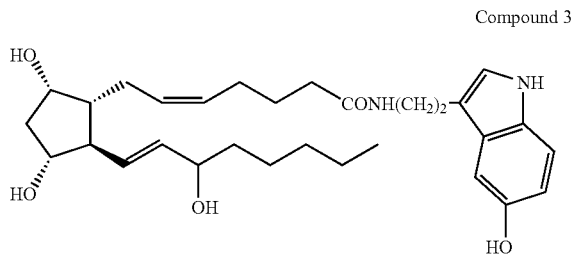

(Z)-7-[(1R,2R,3R,5S)-3,5-Dihydroxy-2-((E)—(S)-3-hydroxy-oct-1-enyl)-cyclopentyl]-hept-5-enoic acid [2-(5-hydroxy-1H-indol-3-yl)-ethyl]-amide Pharmaceutical compositions may be prepared by combining a therapeutically effective amount of at least one compound disclosed herein, or a pharmaceutically acceptable acid addition salt thereof, as an active ingredient, with conventional ophthalmically acceptable pharmaceutical excipients, and by preparation of unit dosage forms suitable for topical ocular use. The therapeutically efficient amount typically is between about 0.0001 and about 5% (w/v), preferably about 0.001 to about 1.0% (w/v) in liquid formulations.

For ophthalmic application, it is useful for solutions to be prepared using a physiological saline solution as a major vehicle. In many cases, it is desirable for the pH of such ophthalmic solutions to be maintained between 6.5 and 7.2 with an appropriate buffer system. The formulations may also contain conventional, pharmaceutically acceptable preservatives, stabilizers and surfactants.

Preservatives that may be used in the pharmaceutical compositions disclosed herein include, but are not limited to, purite, benzalkonium chloride, chlorobutanol, thimerosal, phenylmercuric acetate and phenylmercuric nitrate. A useful surfactant is, for example, Tween 80. Likewise, various vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. One useful chelating agent is edetate disodium, although other chelating agents may also be used in place or in conjunction with it.

The ingredients are usually used in the following amounts:

| Ingredient | Amount (% w/v) |
| --- | --- |
| active ingredient | about 0.001–5 |
| preservative | 0–0.10 |
| vehicle | 0–40 |
| tonicity adjustor | 1–10 |
| buffer | 0.01–10 |
| pH adjustor | q.s. pH 4.5–7.5 |
| antioxidant | as needed |
| surfactant | as needed |
| purified water | as needed to make 100% |

The actual dose of the active compounds of the present invention depends on the specific compound, and on the condition to be treated; the selection of the appropriate dose is well within the knowledge of the skilled artisan.

The ophthalmic formulations disclosed herein are conveniently packaged in forms suitable for metered application, such as in containers equipped with a dropper, to facilitate the application to the eye. Containers suitable for dropwise application are usually made of suitable inert, non-toxic plastic material, and generally contain between about 0.5 and about 15 ml solution.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the appended claims.

EXAMPLE 1

Protection of Prostaglandin $F_{2\alpha}$

A solution of prostaglandin $F_{2\alpha}$ (3.73 g, 10.5 mmol), iodomethane (2.6 mL, 42.0 mmol), and 1,8-diazobicyclo[5.4.0] undec-7-ene (3.1 mL, 21.0 mmol) in acetone (42 mL) was stirred at 23° C. for 24 hours. The reaction was concentrated in vacuo and the residue was diluted with ethyl acetate and washed with HCl (1 N), saturated sodium bicarbonate, and brine. The organic portion was then dissolved in CH$_2$Cl$_2$ (42 mL) with pyridinium p-toluenesulfonate (264 mg, 1.05 mol) and 3,4-dihydro-2H-pyran (5.7 mL, 63.0 mmol), and stirred for 12 hours at room temperature. The reaction was diluted with ethyl acetate and washed with HCl (1 N), saturated sodium bicarbonate, and brine. The organic portion was dried (MgSO$_4$), filtered and concentrated in vacuo. Flash column chromatography (4:1 hexane:ethyl acetate) gave the protected prostaglandin F$_{2\alpha}$ (5.8 g, 89%).

EXAMPLE 2

A solution of the protected prostaglandin F$_{2\alpha}$ (311 mg, 0.513 mmol) in CH$_2$Cl$_2$ (4.5 mL) was treated with triethylamine (290 µL, 2.06 mmol) with stirring and cooled to 0° C. Ethylchloroformate (180 µL, 1.28 mmol) was then added and after 15 minutes the reaction was warmed to room temperature. Dopamine hydrochloride (487 mg, 2.57 mmol) was added and stirred for 16 hours. The reaction was then diluted with ethyl acetate and washed with HCl (1 N), saturated sodium bicarbonate, and brine. The organic portion was dried (MgSO$_4$), filtered and concentrated in vacuo. The residue was diluted with CH$_2$Cl$_2$ (7.5 mL), cooled to 0° C., and triethylamine (0.34 mL, 3.08 mmol) was added. 4-Dimethylaminopyridine (DMAP) was added (20 mg) followed by acetic anhydride (0.14 mL, 1.58 mmol). The reaction was stirred for 16 h, diluted with ethyl acetate, and washed with HCl (1 N), saturated sodium bicarbonate, and brine. The organic portion was dried (MgSO$_4$), filtered and concentrated in vacuo. Flash column chromatography (silica gel, 1:1 hexane:ethyl acetate) gave the tetrahydropyran (THP) protected diacetate.

The diacetate was diluted with methanol (4.5 mL) and PPTs (50 mg) was added and stirred for 16 hours. The solvent was then removed in vacuo, and the residue was diluted with ethyl acetate and washed with HCl (1 N), saturated sodium bicarbonate, and brine. The organic portion was dried (MgSO$_4$), filtered and concentrated in vacuo. Flash column chromatography (silica gel, 19:1 ethyl acetate:methanol) gave acetic acid 2-acetoxy-5-(2-{(Z)-7-[(1R,2R,3R,5S)-3,5-dihydroxy-2-((E)—(S)-3-hydroxy-oct-1-enyl)-cyclopenyl]-hept-5-enoylamino}-ethyl)-phenyl ester (Compound 1) (87 mg, 30%).

EXAMPLE 3

A mixture of acetic acid 2-acetoxy-5-(2-{(Z)-7-[(1R,2R,3R,5S)-3,5-dihydroxy-2-((E)—(S)-3-hydroxy-oct-1-enyl)-cyclopenyl]-hept-5-enoylamino}-ethyl)-phenyl ester (0.57 mg, 0.099 mmol) and aqueous lithium hydroxide (0.5N, 0.8 mL, 0.397 mmol) in tetrahydrofuran (THF) (1.6 mL) was stirred for 16 h. The reaction was diluted with ethyl acetate and acidified with 1 N HCl. The organic portion was separated and washed twice with brine, dried (MgSO$_4$), filtered, and concentrated in vacuo. Flash column chromatography (silica gel, 19:1 ethyl acetate:methanol) gave (Z)-7-[(1R,2R,3R,5S)-3,5-Dihydroxy-2-((E)—(S)-3-hydroxy-oct-1-enyl)-cyclopentyl]-hept-5-enoic acid [2-(3,4-dihydroxy-phenyl)-ethyl]-amide (Compound 2) (7.5 mg, 15%).

EXAMPLE 4

A solution of the protected prostaglandin F$_{2\alpha}$ (500 mg, 0.825 mmol) in CH$_2$Cl$_2$ (4.5 mL) was treated with triethylamine (290 µL, 2.06 mmol) with stirring and cooled to 0° C. Ethylchloroformate (87 µL, 0.907 mmol) was then added and after 15 minutes the reaction was warmed to room temperature. Serotonin hydrochloride (211 mg, 0.99 mmol) was added and stirred for 16 hours. The reaction was then diluted with ethyl acetate and washed with HCl (1 N), saturated sodium bicarbonate, and brine. The organic portion was dried (MgSO$_4$), filtered and concentrated in vacuo. The residue was diluted with methanol and pyridiniump-toluenesulfonate (PPTs) (100 mg) was added and the solution was stirred for 24 hours. The solvent was then removed in vacuo, and the residue was diluted with ethyl acetate and washed with HCl (1 N), saturated sodium bicarbonate, and brine. The organic portion was dried (MgSO$_4$), filtered and concentrated in vacuo. Flash column chromatography (silica gel, 19:1 ethyl acetate:methanol) gave (Z)-7-[(1R,2R,3R,5S)-3,5-Dihydroxy-2-((E)—(S)-3-hydroxy-oct-1-enyl)-cyclopentyl]-hept-5-enoic acid [2-(5-hydroxy-1H-indol-3-yl)-ethyl]-amide (Compound 3) (287 mg, 68%).

EXAMPLE 5

Intraocular pressure studies were carried out for compounds 1–3 by pneumatonometry in dogs (Beagle) of both sexes (10–15 kg). The animals remained conscious throughout the study and were gently restrained by hand. Drugs were administered topically to one eye as a 25 µL volume drop comprising 0.03% drug, 0.1% polysorbate 80:10 mM TRIS, the other eye received 0.1% polysorbate 80:10 mM TRIS. Proparacaine (0.1%) was used for corneal anesthesia during tonometry. Intraocular pressure was determined just before drug administration and at 2, 4 and 6 hours thereafter on each day of the 5 day study. Results are presented in the table below, which demonstrates that the compound disclosed herein are useful in decreasing intraocular pressure. Drug was administered immediately after the first IOP reading.

| Compound | Change in Intraocular Pressure (IOP) | | | | |
|---|---|---|---|---|---|
| | 0 hrs | 2 hrs | 4 hrs | 6 hrs | 24 hrs |
| 1 | 0 | −4.4** | −3.4** | −3.1** | −1.4* |
| 2 | 0 | −3.8* | −3.2** | −3.2** | −1.1* |
| 3 | 0 | −3.2* | −5.8* | −7.6** | −2.2 |

*p < 0.05,
**p < 0.01, according to Student's paired t test

What is claimed is:
1. A compound of the formula

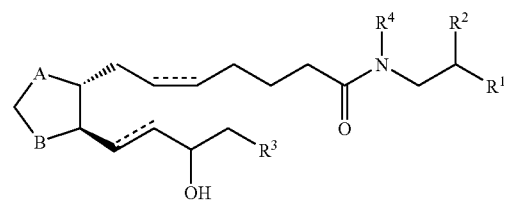

or a salt or ester thereof, wherein said compound is not naturally occurring;

the hatched wedge indicates an α configuration and the solid wedge indicates a β configuration;

the dashed line indicates the presence or absence of a double bond;

A and B are both CHOH, or A is CHOH and B is C=O, or B is CHOH and A is C=O;

$R^1$ is indolyl, or monohydroxy or dihydroxy indolyl;

$R^2$ is OH or H;

$R^3$ is n-butyl, n-pentyl, or n-hexyl; cyclohexyl, Ar, or W—Ar;

wherein Ar is phenyl, naphthyl optionally substituted with 1 to 3 substituents selectd from the group consisting of halogen, methyl, or trifluoromethyl; and W is $CH_2$; and $R^4$ is hydrogen, methyl, ethyl, iso-propyl, or n-propyl.

2. The compound of claim 1 wherein $R^3$ is n-butyl, Ar, or W—Ar, wherein Ar is phenyl, naphthyl, or benzothienyl.

3. The compound of claim 1 wherein $R^3$ is n-butyl, Ar, or W—Ar, wherein Ar is phenyl.

4. The compound of claim 1 wherein $R^3$ is n-butyl or W—Ar, wherein W is O or $CH_2$, and Ar is phenyl.

5. The compound of claim 1 wherein $R^1$ is 5-hydroxyindolyl, $R^2$ is H, and $R^4$ hydrogen.

6. The compound of claim 1 of the formula

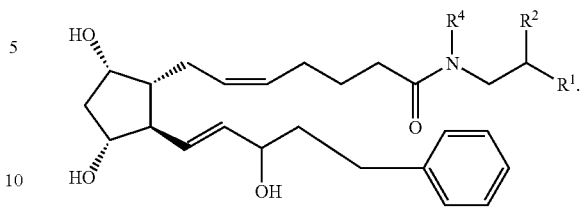

7. The compound of claim 1 of the formula

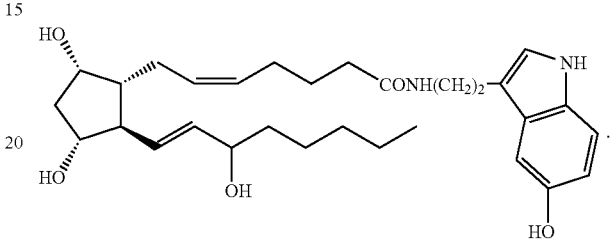

8. An ophthalmic composition comprising a compound of claim 1.

9. A method of treating glaucoma comprising administering to a mammal suffering from glaucoma or ocular hypertension an effective amount of a compound of claim 1.

* * * * *

UNITED STATES PATENT AND TRADEMARK OFFICE
CERTIFICATE OF CORRECTION

PATENT NO. : 7,186,744 B2 Page 1 of 1
APPLICATION NO. : 10/713500
DATED : March 6, 2007
INVENTOR(S) : Woodward et al.

It is certified that error appears in the above-identified patent and that said Letters Patent is hereby corrected as shown below:

On the Title Page, in item (56), under "Other Publications", in column 1, line 5, after "447-449" delete ")".

On the Title Page, in item (56), under "Other Publications", in column 2, line 25, after "1993," insert -- 36, --.

Column 4, line 23, delete "doparnine" and insert -- dopamine --, therefor.

Column 7, line 60. delete "[3H]" and insert -- [$^3$H] --, therefor.

Column 12, line 54, below "herein:" delete "Compound 2" and insert -- Compound 1 --, therefor.

Column 13, line 3, delete "cyclopenyl" and insert -- cyclopentyl --, therefor.

Column 15, line 48, delete "cyclopenyl" and insert -- cyclopentyl --, therefor.

Column 15, line 55, delete "cyclopenyl" and insert -- cyclopentyl --, therefor.

Column 16, lines 13-14, delete "pyridiniump-toluenesulfonate" and insert -- pyridinium p-toluenesulfonate --, therefor.

Column 17, line 18, in Claim 1, delete "selectd" and insert -- selected --, therefor.

Column 17, line 31, in Claim 5, after "R$^4$" insert -- is --.

Signed and Sealed this

Twenty-ninth Day of May, 2007

JON W. DUDAS
*Director of the United States Patent and Trademark Office*